(12) United States Patent
Kukkala et al.

(10) Patent No.: US 6,291,580 B1
(45) Date of Patent: Sep. 18, 2001

(54) POLYURETHANES WITH CARBOXYLATE FUNCTIONALITY FOR HAIR FIXATIVE APPLICATIONS

(75) Inventors: Pravin K. Kukkala, Louisville, KY (US); Sharon P. Lee, Metuchen, NJ (US); Andrew J. Kielbania, Jr., Chalfont, PA (US); Melissa J. Vitale, Plainsboro, NJ (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/340,332

(22) Filed: Jun. 25, 1999

Related U.S. Application Data

(62) Division of application No. 09/028,826, filed on Feb. 24, 1998, now Pat. No. 5,968,494.

(51) Int. Cl.[7] .................................................. C08G 18/65
(52) U.S. Cl. .......................... 524/840; 524/591; 528/49; 528/71; 528/79
(58) Field of Search ................... 524/840, 591; 528/79, 49, 71

(56) References Cited

U.S. PATENT DOCUMENTS

| | | |
|---|---|---|
| 3,350,362 | 10/1967 | Potts et al. .......................... 260/77.5 |
| 3,388,087 | 6/1968 | Dieterich et al. ................... 260/29.2 |
| 3,479,310 | 11/1969 | Dieterich et al. ................... 260/29.2 |
| 3,539,483 | 11/1970 | Keberle et al. ..................... 260/29.2 |
| 3,822,238 | 7/1974 | Blair et al. ...................... 260/75 NK |
| 3,835,081 | 9/1974 | Remley ....................... 260/29.2 TN |
| 3,957,774 | 5/1976 | Kalopissis et al. .............. 260/246 B |
| 3,975,350 | 8/1976 | Hudgin et al. .................. 260/34.4 N |
| 4,066,591 | 1/1978 | Scriven et al. ................ 260/29.2 TN |
| 4,092,286 | 5/1978 | Noll et al. .................... 260/29.2 TN |
| 4,147,679 | 4/1979 | Scriven et al. ................ 260/29.2 TN |
| 4,156,067 | 5/1979 | Gould ................................... 528/73 |
| 4,186,118 | 1/1980 | Reischl et al. ................ 260/29.2 TN |
| 4,657,964 | * 4/1987 | Tai et al. .............................. 524/409 |
| 4,742,095 | 5/1988 | Markusch et al. ................... 523/322 |
| 4,743,673 | 5/1988 | Johnston et al. ....................... 528/60 |
| 4,764,553 | 8/1988 | Mosbach et al. .................... 524/591 |
| 4,798,721 | 1/1989 | Yahagi et al. ......................... 424/70 |
| 4,985,239 | 1/1991 | Yahagi et al. ......................... 424/70 |
| 5,478,562 | 12/1995 | Cauwet et al. ....................... 424/401 |
| 5,538,717 | 7/1996 | La Poterie .............................. 424/61 |
| 5,626,840 | 5/1997 | Thomaides et al. .............. 424/70.11 |
| 5,650,159 | 7/1997 | Lion et al. ............................ 424/401 |

FOREIGN PATENT DOCUMENTS

| | | | |
|---|---|---|---|
| 195 41 326 A1 | 11/1995 | (DE) | ............... C08G/18/83 |
| 195 41 329 A1 | 11/1995 | (DE) | ................. A61K/7/11 |
| 320 218 A2 | 6/1989 | (EP) | ............. C08F/220/56 |
| 0 323 715 A2 | 7/1989 | (EP) | ................. A61K/7/06 |
| 0 451 657 A2 | 10/1991 | (EP) | ............... C08G/18/34 |
| 0 636 361 A1 | 2/1995 | (EP) | ................. A61K/7/48 |
| 0 734 714 A2 | 10/1996 | (EP) | ................. A61K/7/06 |
| 0 734 717 A2 | 10/1996 | (EP) | ................. A61K/7/11 |
| 0 745 373 A1 | 12/1996 | (EP) | ................. A61K/7/06 |
| 0 758 546 A1 | 2/1997 | (EP) | ................. A61K/7/06 |
| 0 773 246 A1 | 5/1997 | (EP) | ............... C08G/18/12 |
| 2 306 490 | 5/1997 | (GB) | ............... C08G/18/32 |
| 8-301733 | 11/1996 | (JP) | ................. A61K/7/11 |
| WO 94/03510 | 2/1994 | (WO) | ............... C08G/18/08 |
| WO 94/13724 | 6/1994 | (WO) | ............... C08G/18/32 |
| WO 96/14049 | 5/1996 | (WO) | ................. A61K/7/06 |
| WO 97/17052 | 5/1997 | (WO) | ................. A61K/7/06 |
| WO 97/17386 | 5/1997 | (WO) | ............... C08G/18/08 |

OTHER PUBLICATIONS

D. Dieterich, "Aqueous Emulsoins, Dispersions and Solutions of Polyurethanes; Synthesis and Properties", *Progress in Organic Coatings*, 9 (1981) 281–340. (No Month).

Rosthauser and Nachtkamp, "Waterborne Polyurethanes", *Adv. Urethane Science and Technology*, 1987, 121–162, (No Month).

Tharanikkarasu and Kim, "Aqueous Dispersions of Polyurethane Ionomers", Department of Polymer Science and Engineering, Pusan National University, Korea, 13th Jan.1997, 26–55.

\* cited by examiner

*Primary Examiner*—Rachel Gorr
(74) *Attorney, Agent, or Firm*—Karen G. Kaiser

(57) ABSTRACT

A polyurethane, soluble or dispersible in water, prepared from organic diisocyanate diols or other isocyanate reactive materials and a 2,2-hydroxymethyl-substituted carboxylic acid diol neutralized with a cosmetically acceptable organic or inorganic base and formulated into a hair fixative composition containing low amounts of volatile organic solvent. The present invention is also directed to a process for the preparation of polyurethanes comprising dispersing the polyurethane after at least 70% of the theoretical isocyanate reaction has taken place, but before completion of the reaction.

4 Claims, No Drawings

POLYURETHANES WITH CARBOXYLATE FUNCTIONALITY FOR HAIR FIXATIVE APPLICATIONS

CROSS-REFERENCE TO RELATED APPLICATIONS

This is a divisional of U.S. patent application Ser. No. 09/028,826, filed Feb. 24, 1998, issued as U.S. Pat. No. 5,968,494.

FIELD OF THE INVENTION

This invention pertains to hair fixative compositions comprising polyurethanes containing pendant free carboxyl groups neutralized with standard cosmetically acceptable bases, and to a process for preparing polyurethanes.

BACKGROUND OF THE INVENTION

Polyurethanes have been used for a wide variety of applications. Since the early 1970's aqueous polyurethane dispersions have expanded in utility. The incorporation of ionic salt groups into the polyurethane prepolymer before dispersing into water greatly facilitates the formation of the aqueous polyurethane dispersion. Aqueous polyurethane dispersion technology has matured considerably; however, the basic polyurethane in the polyurethane dispersion is the result of reacting a diisocyanate, a diol or diamine (polyether, polyester, etc.) and a hydroxyl or diol (or amine analogue) molecule containing an ionic salt group. The ionic salt groups most often used are carboxylic, sulfonic and phosphoric acids (or the base neutralized acids), amine (or acid neutralized amine), or quaternary nitrogen groups. One of the most often used carboxyl reactants is dimethylol propionic acid.

Aqueous polyurethane dispersions have been used extensively as adhesives and coatings on essentially any synthetic or natural substrate such as paper, wood, cotton, leather, wool and hair. Specific applications in the pharmaceutical, cosmetic and hair fixative areas have been disclosed. Recently hair fixative applications have focused upon using hard polyurethanes which have a glass transition, Tg, above about room temperature. These hard, high Tg polyurethanes are used to provide the hold and curl retention necessary for hair fixatives but suffer from unpleasant, hard aesthetic feel on hair and brittleness of the polyurethane which results in flake development, raspy feel, or difficult to comb properties.

Most hair fixative compositions contain a film-forming polymer, which acts as the fixative, and a delivery system, which is usually an alcohol or a mixture of alcohol and water. In the case of aerosol delivery, the delivery system will also contain a propellant, which is typically a volatile hydrocarbon. Due to environmental regulations controlling the emission of volatile organic components (VOCs) into the atmosphere, these alcohol and hydrocarbon delivery systems are becoming less acceptable, and it is foreseen that water will become a greater component in hair fixative compositions. In addition, several different delivery systems for hair fixatives are now utilized, for example hair sprays, both aerosols and pumps, gels and mousses. Hair fixative polymers taught for use in aqueous based systems are known, for example, those disclosed in Japanese publication JP 47-46332. However, many of these exhibit a loss of performance properties in aqueous systems, for example, curl retention and on-hair stiffness are inferior, and in other cases the solution viscosity increases, and if delivered by aerosol, the composition foams at the valve actuator and on the hair. In addition, current systems may also exhibit poor compatibility with aqueous delivery systems. Overall the requirements for hair fixatives have increased. Performance requirements for hair fixatives now demand that the hair fixative polymer maintain a high degree of hold, gloss, curl retention, stiffness, and humidity resistance, but yet have pleasing aesthetics with a natural soft feel with no adhesive tackiness, no raspiness or brittle feel, no flake development and yet be readily removable. These factors have prompted the search for better performing hair fixative polymers that are soluble or dispersible in aqueous or in low VOC systems, that is, systems containing 80% or less VOCs. Current systems do not provide this required balance of properties.

U.S. Pat. No. 5,626,840 discloses polyurethanes prepared from an organic diisocyanate, a diol with a number average molecular weight greater than 1000, and a 2,2-hydroxymethyl-substituted carboxylic acid which are neutralized with a cosmetically acceptable organic or inorganic base and formulated into a hair fixative composition containing low amounts of volatile organic solvent.

SUMMARY OF THE INVENTION

The invention is directed to a process for preparing polyurethanes and to the use of polyurethanes in hair fixative compositions. The hair fixative composition of the present invention comprises a water soluble or dispersible polyurethane that, despite its solubility or dispersibility in water, also demonstrates good hold and flexibility, good compatibility with aerosol propellants, good spray characteristics, curl retention, stiffness, nontackiness, and forms a clear, transparent, glossy film that is easily removable with water (good rinsability) or with water and shampoo.

The hair fixative composition comprises (a) an effective amount of the polyurethane to perform as a hair fixative in an all water, alcohol-water, or allorganic system; (b) an effective amount of a cosmetically acceptable organic or inorganic base to neutralize a sufficient proportion of the available carboxyl groups on the polyurethane to make the polyurethane soluble or dispersible in water or in a mixture of water and an organic diluent; and (c) a diluent comprising (i) water, or (ii) water and 0 to about 90% by weight of an organic solvent, based on the weight of the solvent, or (iii) organic solvent.

In order to achieve the balance of required properties, we have found that two different components with active hydrogen atoms, one contributing rigidity and the other contributing flexibility to the polymer backbone, in addition to the carboxylic acid diol, are needed for the preparation of the polyurethane. Prior art has neither taught nor recognized the need for multiple polyols in the preparation of polyurethane hair fixatives with the above balance of properties.

The polyurethane is a fully reacted carboxylated polyurethane prepared as the reaction product of (i) one or more 2,2-hydroxymethyl-substituted carboxylic acids present in an amount to give 0.35 to 2.25 milliequivalents of carboxyl functionality per gram of polyurethane, (ii) 5 to 90% by weight, based on the weight of the polyurethane, of one or more organic components, other than the 2,2-hydroxymethyl-substituted carboxylic acids, each having at least two active hydrogen atoms, and (iii) one or more organic diisocyanates present in a sufficient amount to react with the active hydrogens of the 2,2-hydroxymethyl-substituted carboxylic acids and the organic components, excepting the hydrogen on the carboxylate of the 2,2-hydroxymethyl-substituted carboxylic acid. Properties can be further enhanced by chain extension and chain termination.

The hair fixative composition may be used in sprays, aerosols, pumps, gels, mousses and lotions. In aerosol systems, the hair fixative composition will further comprise up to 60% by weight of a propellant based on the weight of the total hair fixative composition.

The present invention is also directed to a process for preparing polyurethanes wherein the dispersion is accomplished after at least 50%, but before completion, of the theoretical isocyanate reaction has taken place.

DETAILED DESCRIPTION OF THE INVENTION

The polyurethanes suitable for use in hair fixative formulations according to this invention are fully reacted carboxylated polymers. These polyurethanes are used in an effective amount to achieve the desired balance of properties, such as hold, curl retention, stiffness, and humidity resistance, pleasing esthetics with a natural soft feel with no adhesive tackiness, no raspiness, or brittle feel, no flake development and having rinsability. They are preferably present in amounts from 1 to 20% by weight of the hair fixative composition, and more preferably in amounts from 1 to 10% by weight.

The incorporation of the 2,2-hydroxymethyl-substituted carboxylic acid introduces pendant carboxylic acid groups into the polymer chain, which after neutralization render the polyurethane soluble or dispersible in water or in mixtures of water with other polar solvents. Using these polyurethanes as the active ingredient, hair fixative formulations can be made that have a high solids content with low viscosity. A high solids content supplies an effective amount of polymer to the hair in a minimum amount of solvent to obtain good holding power. Low viscosity permits effective atomization at the spray nozzle. Thus, a hair fixative product suitable for use in either aerosol or non aerosol formulations can be achieved. However, in some cases, when high amounts of 2,2-hydroxymethyl-substituted carboxylic acids are incorporated to achieve good rinsability, this can be detrimental to flexibility, soft feel, formulation compatibility, and can increase flake development and raspiness.

The 2,2-hydroxymethyl-substituted carboxylic acids are represented by the formula

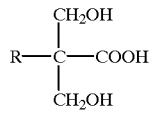

in which R represents hydrogen, or $C_1$–$C_{20}$ alkyl, preferably $C_1$–$C_8$ alkyl. Specific examples include 2,2-di(hydroxymethyl)acetic acid, 2,2-di(hydroxymethyl)propionic acid, 2,2-di-(hydroxy-methyl)butyric acid, 2,2-di(hydroxymethyl)pentanoic acid, and the like. The preferred acid is 2,2-di(hydroxymethyl)propionic acid. The 2,2-hydroxymethyl-substituted carboxylic acids are present in an amount to give 0.35 to 2.25, preferably 0.5 to 1.85, milliequivalents of carboxyl functionality per gram of polyurethane, and in general this is about 3 to 30% by weight of the polyurethane polymer.

The organic components that are reactive with isocyanate and that may be used for the preparation of the polyurethane polymers of this invention have at least two active hydrogen atoms (as determined by the Zerewitinoff method). The active hydrogen atoms are usually attached to oxygen, nitrogen or sulfur atoms. The organic components will be present in an amount of 10 to 90% by weight of the polyurethane, preferably in an amount of 15 to 70% by weight and may have a molecular weight less than 1000. Preferably, these components will be linear so that gelling during polymerization is prevented, but small amounts of non-linear components may be used to enhance properties provided their use does not cause gelling.

One or more different organic components with active hydrogens are used. Alternatively, these different components could be combined into one component. These organic components will be designated components (A), (B) and (C).

Component (A) is a polymer with at least two active hydrogen atoms having a Tg less than 5° C., preferably less than –10° C. Tg. Specifically, component (A) may be, but is not limited to, a poly(alkylene oxide), e.g., a polyethoxylate, a polypropoxylate, a polyethoxylate/propoxylate, polymethylene oxide, polybutylene oxide, polyesterdiols, polyolefin diols, poly(meth)acrylate diols, polysiloxanediamines or polysiloxanediols.

Component (B), comprises a cyclic ring structure. Specifically (B) includes active hydrogen components containing 5 to 14-membered rings, wherein the rings may be heterocyclic, aliphatic, aromatic, cyclic, alicyclic, and/or spiro rings. Examples of such rings include cyclohexyl, cyclopentyl, norbornyl, phenyl, biphenyl, phenyl ether, Bisphenol A, hydrogenated bisphenol A, morpholino, pyrrolidine, piperidine, pyridine, pyrrole, tetrahydropyran, furan, oxazole. Also included are the aromatic diols and their saturated hydrocarbon analogs disclosed in U.S. Pat. Nos. 3,477,990 and 3,948,855. These rings are substituted with zero to sixteen alkoxylate units. Exemplary components include the Synfac® 8000 series which is available from Milliken Chemicals, the Atlas® G-1600 series which is available from ICI Surfactants and Macol® materials which are available from BASF.

Component (C) may be used in place of or in addition to the combination of organic components (A) and (B), in addition to the DMPA, and optionally other organic components containing active hydrogen atoms. Component (C) may be any of the cyclic ring structures described above with respect to component (B), however substituted with greater than sixteen alkoxylate units.

The ring structures comprising components (B) and (C) can be substituted with H or with lower alkyl substituents of 1 to 4 carbon atoms. To prevent unwanted side reactions, crosslinking and gelling of the polyurethane, preferably there is no acid substitution on the rings.

These one or more organic components with active hydrogens component of the present invention may be one or more of A, B, or C, specifically (A)+(B); (A)+(C); (B)+(C); (A)+(B)+(C); or (C).

In preparing the polyurethanes, the organic components (A), (B) and (C) can be used in any combination in which each component comprises 5 to 90% of the polyurethane composition. For example, (A) and (B) may comprise 5 to 90% by weight of the polyurethane, and (C) may comprise 0 to 90% by weight of the polyurethane. In a preferred embodiment, the polyurethane will have a Tg value less than about 5° C.

In one embodiment, the polyurethane is prepared from a major amount of (A) and (B), having molecular weights less than 1000. In another embodiment, the polyurethane is prepared from a major amount of (A) and (B), having molecular weights greater than 1000.

In preparing the polyurethane polymer, in addition to the organic component having at least two active hydrogen atoms, which in many cases is a high molecular weight component, it may be desirable to chain extend the polymer using another organic component also having active hydrogen atoms. Typical chain extending agents include water, saturated or unsaturated glycols, such as, ethylene glycol, diethylene glycol, triethylene glycol and the like; amino alcohols, such as, ethanolamine, propanolamine, butanolamine, and the like; mono- and dialkoxylated aliphatic, cycloaliphatic, aromatic and heterocyclic primary amines, such as, N-methyldiethanolamine, N-oleyl diethanolamine, N-cyclohexyl diisopropanolamine, N,N-dihydroxyethyl-p-toluidine, N,N-dihydroxy-propyinaphthylamine and the like; amines, such as ethylene diamine, diethylene tetramine, triethylenetetramine, piperazine, N-N-bis-gamma-aminopropyl-N-methyl-amine, taurine, silicone diamine, Jeffamines® and the like; ethyoxiated polyamines such as Jeffamines® D and T series; carboxylic acids including aliphatic, cycloaliphatic, aromatic and heterocyclic dicarboxylic acids, such as, oxalic acid, malonic acid, succinic acid, glutaric acid, adipic acid, sebacic acid, terephthalic acid, 1,5-dicarboxylic naphthalic acid, maleic acid, fumaric acid, diglycolic acid, quinolinic acid, lutidinic acid and the like; amino carboxylic acids, such as, glycine, lysine, aspartic acid, iminodiacetic acid, alpha and beta-alanine, 6-aminocaproic acid, 4-aminobutyric acid, p-aminobenzoic acid, 5-aminonaphthoic acid and the like; and amino acids such as glucamine, maltoamine and lactamine and the like.

Chain extenders may also be saccharide amines based on reducing sugars or those composed of glycosyl units connected by glycosidic linkages which are disclosed in U.S. Pat. No. 5,494,602. They can be linear or branched, and they may be composed of a single type of glycosyl unit or they may be composed of two or more different types of glycosyl units. Exemplary saccharides according to the present invention include, without limitation, starches, hydrolyzed starches, glucose, galactose, maltose, lactose, maltodextrins, corn syrup solids, cellulose, hydrolyzed cellulose, dextran, hydrolyzed dextran, guar gum, hydrolyzed guar gum, locust bean gum and hydrolyzed locust bean gum. Such starches include, for example, corn, potato, tapioca and rice starches. The saccharides used to prepare the polymers of the present invention are exemplified in U.S. Pat. No. 5,494,602, which is incorporated herein by reference.

The polyurethane polymer may also be chain terminated. Typical chain terminating agents include ethanol, isopropanol, taurine, and the like. Also included are amino acids such as glucamine, maltamine, lactamine and the like.

The organic polyisocyanates or mixtures of polyisocyanates that are reacted with the organic component are aliphatic or aromatic polyisocyanates, or mixtures of those. The polyisocyanates are preferably diisocyanates in order to result in a linear polymer, although minor amounts of trifunctional isocyanates may be used in conjunction with the diisocyanates. The isocyanate will be present in a sufficient amount to react with the active hydrogens of the 2,2-hydroxymethyl-substituted carboxylic acid and the organic components, excepting the hydrogen on the carboxylate of the 2,2-hydroxymethyl-substituted carboxylic acid. This amount will vary depending on the amounts of the carboxylic acid and organic components.

Exemplary diisocyanates include, but are not limited to, methylene dip-phenyl diisocyanate, methylene-bis(4-cyclohexylisocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 4,4'-dibenzyldiisocyanate, 1,3-phenylene diisocyanate, 1,4-phenylene diisocyanate, mixtures of 2,4- and 2,6-toluene diisocyanate, 2,2'-dichloro-4,4'-diisocyanato diphenylmethane, 2,4-dibromo-1,5-diisocyanato naphthalene, butane-1,4-diisocyanate, hexane-1,6-diisocyanate, cyclohexane-1,4-diisocyanate, bis(1-isocyanato-1-methylethyl)-benzene, and trimethylhexamethylenediisocyanate.

If it is desired not to chain extend the polymer, the reaction of the diisocyanate with the organic component having two active hydrogen atoms is quenched by the addition of a monofunctional active hydrogen-containing component to consume any residual isocyanate functionality. Examples of these quenching components are well known in the art; for these systems, such as monofunctional alcohols, monofunctional amines, and monofunctional low molecular weight polymers. The preferred quenching component is ethanol.

The urethane polymerization is carried out in the reaction medium with or without typical urethane reaction catalysts known in the art. Suitable catalysts include dibutyl tin dilaurate; the stannous salts of carboxylic acids having from 2 to 18 carbon atoms, such as, stannous laurate, stannous stearate, stannous acetate, stannous butyrate, stannous octoate and the like, and mixtures of those. Other suitable catalysts include dibutyl tin oxide, dibutyl tin sulfide, lead resinate, lead benzoate, lead salicylate, lead 2-ethyl hexoate, lead oleate, iron acetyl acetonate, cobalt benzoate, tetra (2-ethyl hexyl) titanate, tetra butyl titanate, and the like. Many other components accelerate the reaction of a hydroxyl or other groups with an isocyanate in preference to certain other reactions of the isocyanate group, and any of these components may be used. Those skilled in the art will choose a specific catalyst to confer desired characteristics to individual urethane reactions. The preceding specific components are the preferred components and are given for the purpose of illustration and not limitation. In addition, any suitable tertiary amine may be used alone or with the metallic catalyst, for example, triethylene diamine, N-ethyl morpholine, N-methyl morpholine, or 4-dimethyl amino ethyl piperazine, triethylamine, diazabicyclooctane.

The polymerization is carried out according to polyurethane polymerization techniques known in the art. With respect to the proportion of reactants, the reactants should be selected so that the molar ratio of the isocyanate groups to active hydrogen atoms is between 0.5:1 and 2:1, also referred to herein as the isocyanate/hydroxyl ratio. These polymerizations may be either solvent-free or may be carried out in the presence of solvent. In addition, the polymerization may be carried out in the presence of surfactant or may be surfactant free. In systems where a solvent is use, techniques commonly known in the art may be used to remove the solvent, e.g. steam distillation, vacuum stripping. Exemplary polymerizations and reaction conditions are given in the examples. Other suitable procedures are described in D. Dietrich, *Progress in Organic Coatings*, 9, 281 (1981), "Aqueous Emulsions, Dispersions and Solutions of Polyurethanes: Synthesis and Properties," and in J. W. Rosthauser & K. Nachtkamp, *Adv. Urethane Science & Technology*, p 121 (1987), "Waterborne Polyurethanes", and in K. Tharanikkarasu and B. K. Kim in *Progress in Rubber Plastics Technology*, 13, p. 26 (1997).

In carrying out the polymerization processes described above, for both solvented and solvent-free processes, we have found that it is useful to perform the dispersion in water prior to the point where the full theoretical reaction of the isocyanate groups has been achieved. Preferably, the dispersion is accomplished after at least 50%, but before completion, of the theoretical isocyanate reaction has taken place; most preferably at least 70%. Standard analytical techniques, known in the art, can be used to monitor the extent of isocyanate reaction in this process, for example, isocyanate titration or other spectroscopic methods. In addition, in some cases, the slow addition of the neutralizing base has been found to facilitate the polymerization process, for example, to avoid exotherms. This polymerization process can be used to advantage particularly in systems where the isocyanate/hydroxyl ratio is less than 1, preferably where the isocyanate/hydroxyl ratio is 0.8 to 0.99. This facilitates the aqueous dispersion step by avoiding excessively high viscosity in the prepolymer, and has the advantage of allowing chain termination and/or chain extension to occur, as in systems where the isocyanate/hydroxyl ratio is greater than 1. This process can provide performance benefits to the hair fixative composition.

In most cases, the polyurethanes are either chain extended or chain terminated. In addition to polyurethanes, the polymeric hair fixative compositions can be polyureas or thiol analogues, particularly in cases where the isocyanate-reactive groups are diamines or thiols or chain extended with water, amine, or alcohol reactants.

This process is not limited to the preparation of polyurethanes for hair care compositions, but may be used to prepare any type of polyurethane for any application, including for example, coatings, fibers, adhesives, sizing agents, etc.

The carboxylated polyurethanes are neutralized by the standard cosmetically acceptable bases known and used in the art, and these may be used singly or in combination. The preferred levels of neutralization is greater than 30%, and in some cases greater than a stoichiometric amount of neutralant, may be used depending on the acidity of the polymer. The preferred bases are sodium hydroxide, potassium hydroxide, 2-amino-2-methyl-1-propanol, histidine, tris(hydroxymethyl)aminomethane, triisopropanolamine, stearamine, triethanolamine and triethylamine. The choice of the base and the degree of neutralization also affect the flexibility of the resultant hair fixative when sprayed on the hair, giving a soft or a hard hold. One or more of the bases may be used, and the choice of which base or bases to utilize and the degree of neutralization required to achieve flexibility is within the expertise of one skilled in the art.

The hair fixative polyurethane of the present invention can be used with or without other hair fixative polymers known in the art such as vinyl acetate/crotonates/vinyl neodecanoate copolymer, octylacrylamide/acrylates/butylaminoethyl methacrylate copolymer, vinyl acetate/crotonates, polyvinyl-pyrrolidone (PVP), polyvinylpyrrolidone/vinyl acetate copolymer, PVP/acrylates copolymer, vinyl acetate/crotonic acid/vinyl propionate, acrylates/acrylamide, acrylates/octylacrylamide, acrylates copolymer, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinyl-caprolactam/PVP/dimethylaminoethyl methacrylate, vinyl acetate/alkylmaleate half ester/N-substituted acrylamide terpolymers, vinyl caprolactam/vinylpyrrolidone/methacrylamidopropyl trimethylammonium chloride terpolymer, methacrylates/acrylates copolymer/amine salt, polyvinylcaprolactam, other polyurethanes and others. The ratio of the hair fixative polymers in such a blend, would vary depending on the desired performance and can be adjusted by those skilled in the art.

Neutralization renders the polymers soluble or dispersible in water for easy formulation into aqueous hair sprays (and thus contributes to removability). The neutralized polymers can be formulated solely in water as the solvent, or the diluent system can be a blend of polar organic solvent and water, or could be solely an organic solvent. Typically, the organic solvent will be an alcohol or ketone. Particularly suitable solvents are low boiling alcohols that are compatible with other components in the hair fixative composition, for example, $C_1$–$C_4$ straight or branched chain alcohols. Exemplary polar solvents are ethanol, propanol, isopropanol, butanol, acetone, dimethylether, methyl ethyl ketone, methyl acetate and dimethoxymethane.

Hair fixative compositions that are intended to be delivered in an aerosol system additionally will require a propellant. While any of the known propellants may be used in these compositions, preferred propellants include the hydrocarbons, particularly the lower boiling hydrocarbons such as $C_3$–$C_6$ straight and branched chain hydrocarbons, for example, propane, butane, isobutane and mixtures of those. Other preferred propellants include the ethers, such as dimethyl ether; hydrofluorocarbons, such as, 1,1-difluoroethane; and the compressed gases, such as nitrogen, air and carbon dioxide. The amount of propellant used in the hair fixative compositions of this invention may vary from about 0 to 60% by weight of the hair spray composition and preferably from about 0 to 40% by weight, based on the weight of the total composition.

An important consideration in determining the amount of organic solvent, or organic solvent and propellant, to be used in the hair fixative composition is the total amount of volatile organic component (VOC) content, and any upper limit of VOC content that may be mandated by environmental regulations. While these compositions may have a wide range of VOC content, from completely aqueous to completely anhydrous, due to current environmental regulations it is preferred that there be less than about 80%, more preferred less than about 55%, and most preferred less than about 20% by weight VOC content, based on the weight of the composition. The balance of the hair fixative composition will be water and the polyurethane.

Optional conventional additives may also be incorporated into the hair fixing composition of this invention to provide certain modifying properties to the composition. Included among these additives are plasticizers, such as glycerine, glycol and phthalate esters; silicones; emollients, lubricants and penetrants, such as lanolin components; fragrances and perfumes; UV absorbers; dyes and other colorants; thickeners; anticorrosion agents; detackifying agents; combing aids; antistatic agents; preservatives; and foam stabilizers. These additives are present in small, effective amounts to accomplish their function, and generally will comprise from about 0.1 to 10% by weight each, and from about 0.1 to 20% by weight total, based on the weight of the composition.

The resulting hair fixative compositions exhibit all of the characteristics required of such a product in systems ranging from completely aqueous to completely anhydrous. The compositions may be used in cosmetic applications, particularly in hair fixatives such as aerosol sprays, pumps, mousses, lotions, and gels.

The following examples are illustrative of the present invention and are not intended to limit the scope of the present invention in any way.

EXAMPLES

Preparation of Polyurethanes

Example 1

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 60° C. and 64 g acetone followed by 125 g isophorone diisocyanate were added. The mixture was heated to 77° C. and allowed to react for 45 minutes. Finally, 39.5 grams triethylamine was added, and the prepolymer was dispersed with vigorous agitation into 613 g of water. An additional 5.4 g of triethylamine was then added. The resulting dispersion was stable, and the dried polymer exhibited a Tg of −7° C. (DSC).

Example 2

A 2 liter reaction vessel, equipped with an agitator, heating mantle, and condenser, and nitrogen purge was charged with 76 g poly(propylene glycol) of 1025 molecular weight, and 67.3 g Synfac® 8009 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 60° C. and 30 g acetone followed by 125 g isophorone diisocyanate were added. The reactants were heated to 77° C. and allowed to react for 1 hour. After 1 hour, 39.5 grams triethylamine was added, and the prepolymer was dispersed with vigorous agitation into 783 g of water. Finally, an additional 5.4 g of triethylamine was added.

Example 3

A 2 liter reaction vessel, equipped with an agitator, heating mantle, and condenser, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 48 g dimethylol propionic acid was added and allowed to disperse for 10 minutes. The mixture was cooled to 40° C. and 66 g acetone followed by 133 g isophorone diisocyanate were added. After stirring for 10 minutes, 39.5 g of triethylamine was added dropwise over 45 minutes. The reaction temperature was brought to 60° C. The reaction was allowed to proceed for a further 40 minutes at 60° C. The prepolymer was then dispersed with vigorous agitation in 179 g water in which 44.5 g Jeffamine® M-1000 had been predissolved. A further 418 g of water was used to dilute the dispersion. The resulting stable white dispersion was then steam-treated to remove acetone.

Example 4

A 2 liter reaction vessel, equipped with an agitator, heating mantle, and condenser, and nitrogen purge was charged with 67 g poly(propylene glycol) of 1025 molecular weight, 26.8 g poly(propylene glycol) of 425 molecular weight, and 21 g Synfac® 8009(Milliken Chemicals). The mixture was heated to 120° C. for 30 minutes and then cooled to 80° C. To the mixture, 72 g dimethylol propionic acid was added and allowed to disperse for 10 minutes. The mixture was cooled to 40° C. and 177 g methylene-bis(4-cyclohexylisocyanate) was added. After stirring for 10 minutes, 60 g of triethylamine was added dropwise over 1 hour. 30 g acetone was also added. The reaction temperature was brought to 60° C. The reaction was allowed to proceed for a further 20 minutes at 60° C. The prepolymer was then dispersed in 79 g water with vigorous agitation. An additional 613 g of water was used to dilute the dispersion. The resulting stable white dispersion was then steam-treated to remove acetone.

Example 5

A 2 liter reaction vessel, equipped with an agitator, heating mantle, and condensor, and nitrogen purge was charged with 152 g poly(propylene glycol) of 1025 molecular weight, and 84 g Synfac® 8031(Milliken Chemicals). The mixture was heated to 120° C. for 30 minutes and then cooled to 80° C. To the mixture, 96 g dimethylol propionic acid was added and allowed to disperse for 10 minutes. The mixture was cooled to 70° C. and 266.4 g isophorone diisocyanate were added. The mixture was heated to 80° C. and allowed to react for 90 minutes, until the level of NCO was 4.3% (after 71.3% of the isocyanate reaction had taken place). Finally, 79.74 grams triethylamine was added, and the prepolymer was dispersed with vigorous agitation into 1196.8 g of water. An additional 10.87 g of triethylamine was then added followed by 250 g of water. The resulting dispersion was stable at 25.9% solids, at a viscosity of 30 cps and at a pH of 8.8.

Example 6

A 2 liter reaction vessel, equipped with an agitator, heating mantle, and condenser, and nitrogen purge was charged with 76 g poly(propylene glycol) of 1025 molecular weight, and 67.3 g Synfac® 8009 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 70° C. and 125 g isophorone diisocyanate was added. The reactants were heated to 80° C. and allowed to react for about ninety minutes. The reaction mixture was cooled to about 65° C. and 39.5 grams triethylamine was then added, and the prepolymer was dispersed with vigorous agitation into 688.1 g of water. Finally, an additional 5.4 g of triethylamine was added. The final solids was 29.9%, pH 7.8 and viscosity of 95 cps.

Example 7

A 2 liter reaction vessel, equipped with an agitator, heating mantle, and condenser, and nitrogen purge was charged with 152 g poly(propylene glycol) of 1025 molecular weight, and 84 g Synfac® 8031(Milliken Chemicals). The mixture was heated to 120° C. for 30 minutes and then cooled to 80° C. To the mixture, 96 g dimethylol propionic acid was added and allowed to disperse for 10 minutes. The mixture was cooled to 65° C. and 266.4 g isophorone diisocyanate was added. The reaction was allowed to rise to a temperature of about 80° C. After one hour, 0.5 g of dibutyl tin dilaurate was added. The reaction was allowed to continue for about 30 more minutes. The reaction mixture was cooled to about 65° C. and 79.74 grams triethylamine was then added. The prepolymer was then dispersed with vigorous agitation in 359 g water in which 89 g Jeffamine® M-1000 had been predissolved. A further 837.8 g of water was used to dilute the dispersion. This was followed by the addition of 10.87 g of triethylamine. The resulting stable dispersion had a solids of 36%, viscosity of 126 cps and a pH of 8.4.

Example 8

A 2 liter reaction vessel, equipped with an agitator, heating mantle, and condensor, and nitrogen purge was charged with 67 g poly(propylene glycol) of 1025 molecular weight, 26.8 g poly(propylene glycol) of 425 molecular weight, and 21 g Synfac® 8009(Milliken Chemicals). The mixture was heated to 120° C. for 30 minutes and then cooled to 80° C. To the mixture, 72 g dimethylol propionic acid was added and allowed to disperse for 10 minutes. The mixture was cooled to 65° C. and 177 g methylene-bis(4-cyclohexylisocyanate) was added. The reaction temperature was then raised to about 80° C. and maintained for about 90 minutes at this temperature, followed by the addition of 59.8 g of triethylamine. The prepolymer was then dispersed in 79 g water with vigorous agitation. A further 369 g of water was used to dilute the dispersion. The resulting stable dispersion was initially foamy and then became translucent after the foam disappeared.

Example 9

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 48 g dimethylol propionic acid was added and allowed to disperse for 10 minutes. The mixture was cooled to 70° C. and 266.4 g isophorone diisocyanate was added followed by the addition of 0.2 g of dibutyl tin dilaurate. The mixture was heated to 80° C. and allowed to react for about one hour. The prepolymer was cooled to 55° C. 30 g of Pluronic® F108 was dissolved in 90 g of acetone and added to the reaction vessel. The mixture was dispersed with vigorous agitation into 440 g of water. The acetone was then removed by vacuum distillation. The resulting dispersion was stable at 43.1% solids, at a viscosity of less than 50 cps.

Example 10

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 48 g dimethylol propionic acid was added and allowed to disperse for 10 minutes. The mixture was cooled to 65° C. and 133.2 g isophorone diisocyanate was added. The reaction was allowed to rise to a temperature of about 80° C. After one hour, 0.2 g of dibutyl tin dilaurate was added. The reaction was allowed to continue for another hour and a half. The reaction mixture was cooled to about 55° C. 44.5 g of Jeffamine® M-1000 was dissolved in 35 g of acetone and added to the reaction vessel. The mixture was dispersed with vigorous agitation into 300 g of water. The acetone was then removed by vacuum distillation. The resulting dispersion was stable at 50.6% solids, at a viscosity of less than 1000 cps.

Example 11

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 65° C. and 133.2 g isophorone diisocyanate was added. The reaction was allowed to rise to a temperature of about 80° C. The reaction was allowed to continue for about one hour and a half. The reaction mixture was cooled to about 65° C. and 39.46 grams triethylamine was then added. The prepolymer was then dispersed with vigorous agitation in 179.2 g water in which 22.25 g Jeffamine® M-1000 and 22.5 g of reductively aminated maltodextrrin, saccharide monoamine (molecular weight 2560) had been predissolved. A further 418.2 g of water was used to dilute the dispersion. This was followed by the addition of 5.38 g of triethylamine. The resulting stable dispersion had a solids of 36.9%, viscosity of 165 cps and a pH of 7.9.

Example 12

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 65° C. and 133.2 g isophorone diisocyanate was added. The reaction was allowed to rise to a temperature of about 80° C. The reaction was allowed to continue for about two hours and a half. The reaction mixture was cooled to about 65° C. and 39.46 grams triethylamine was then added. The prepolymer was then dispersed with vigorous agitation in 179.2 g water in which 44.5 g of reductively aminated maltodextrrin, saccharide monoamine (molecular weight 2560) had been predissolved. A further 418.2 g of water was used to dilute the dispersion. This was followed by the addition of 5.38 g of triethyl amine. The resulting stable dispersion had a solids of 36%, viscosity of 190 cps and a pH of 8.

Example 13

A 2 liter reaction vessel, equipped with an agitator, heating mantle, and condensor, and nitrogen purge was charged with 76 g poly(propylene glycol) of 1025 molecular weight, and 42 g Synfac® 8031(Milliken Chemicals). The mixture was heated to 120° C. for 30 minutes and then cooled to 80° C. To the mixture, 48 g dimethylol propionic acid was added and allowed to disperse for 10 minutes. The mixture was cooled to 65° C. and 133.2 g isophorone diisocyanate was added. The reaction was allowed to rise to a temperature of about 80° C. After one hour, 0.25 g of dibutyl tin dilaurate was added. The reaction was allowed to continue for about one hour and a half. The reaction mixture was cooled to about 65° C. and 35.8 grams triethylamine was then added. The prepolymer was then dispersed with vigorous agitation in 179.2 g water in which 5.92 g of iminodiacetic acid had been predissolved after neutralization with triethylamine. A further 418.9 g of water was used to dilute the dispersion. This was followed by further addition of 100 g of water. The resulting stable dispersion had a solids of 31.1%, viscosity of 52 cps and a pH of 8.

Example 14

A 2 liter reaction vessel, equipped with an agitator, heating mantle, and condenser, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 65° C. and 133.2 g isophorone diisocyanate was added. The reaction was allowed to rise to a temperature of about 80° C. The reaction was allowed to continue for about two hours. The reaction mixture was cooled to about 65° C. and 39.46 grams triethylamine was then added. The prepolymer was then dispersed with vigorous agitation in 179.2 g water in which 22.5 g Jeffamine® M-1000 and 5.29 g of iminodiacetic acid had been predissolved. A further 418.2 g of water was used to dilute the dispersion. This was followed by the addition of 5.38 g of triethyl amine. The resulting stable dispersion had a solids of 35.6%, viscosity of 110 cps and a pH of 7.1.

Example 15

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 65° C. and 133.2 g isophorone diisocyanate was added. The reaction was allowed to rise to a temperature of about 80° C. The reaction was allowed to continue for about two hours. The reaction mixture was cooled to about 65° C. and 39.46 grams triethylamine was then added. The prepolymer was then dispersed with vigorous agitation in 179.2 g water in which 5.0 g taurine had been predissolved. A further 418.2 g of water was used to dilute the dispersion. This was followed by the addition of 5.38 g of triethyl amine. The resulting stable dispersion had a solids of 34.8%, viscosity of 150 cps and a pH of 7.1.

Example 16

A 2 liter reaction vessel, equipped with an agitator, heating mantle, and condensor, and nitrogen purge was charged with 76 g poly(propylene glycol) of 1025 molecular weight, and 42 g Synfac® 8031 (Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 65° C. and 133.2 g isophorone diisocyanate was added. The reaction was allowed to rise to a temperature of about 80° C. The reaction was allowed to continue for about two hours. The reaction mixture was cooled to about 65° C. and 39.46 grams triethylamine was then added. The prepolymer was then dispersed with vigorous agitation in 89.6 g water in which 5.0 g of taurine was dissolved. This was immediately followed by the addition of 89.6 g of water in which 22.25 g Jeffamine® M-1000 had been predissolved. A further 418.2 g of water was used to dilute the dispersion. This was followed by the addition of 5.38 g of triethylamine. The resulting stable dispersion had a solids of 35.2%, viscosity of 65 cps and a pH of 8.4.

Example 17

A 2 liter reaction vessel, equipped with an agitator, heating mantle, and condenser, and nitrogen purge was charged with 100 g poly(propylene glycol) of 1025 molecular weight, 20 g poly(propylene glycol) of 425 molecular weight, and 5 g hydrogenated bisphenol A (Milliken Chemicals). The mixture was heated to 120° C. for 30 minutes and then cooled to 80° C. To the mixture, 72 g dimethylol propionic acid was added and allowed to disperse for 10 minutes. The mixture was cooled to 40° C. and 83 g acetone followed by 177 g methylene-bis(4-cyclohexylisocyanate) was added. After stirring for 10 minutes, 60 g of triethylamine was added dropwise over 1 hour. The reaction temperature was brought to 60° C. The reaction was allowed to proceed for a further 70 minutes at 60° C. The prepolymer was then dispersed in 79 g water with vigorous agitation. A further 613 g of water was used to dilute the dispersion.

Example 18

A 2 liter reaction vessel, equipped with an agitator, heating mantle, and condensor, and nitrogen purge was charged with 76 g poly(propylene glycol) of 1025 molecular weight, and 50.5 g Synfac 8031(Milliken Chemicals). The mixture was heated to 120° C. for 30 minutes and then cooled to 80° C. To the mixture, 36.1 g of cyclohexane dimethanol and 47.5 g dimethylol propionic acid was added and allowed to disperse for 10 minutes. The mixture was cooled to 65° C. and 125 g isophorone diisocyanate was added. The reaction was allowed to rise to a temperature of about 80° C. The reaction was allowed to continue for about one hour. The reaction mixture was cooled to about 65° C. and 39.46 grams triethylamine was then added. The prepolymer was then dispersed with vigorous agitation in 467 g water. The resulting stable dispersion was foamy and white.

Example 19

A 2 liter reaction vessel, equipped with an agitator, heating mantle, and condensor, and nitrogen purge was charged with 76 g poly(propylene glycol) of 1025 molecular weight, and 42 g Synfac® 8031(Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 60° C. and 64 g acetone followed by 140 g 4,4'-methylenebis(phenylisocyanate) were added. The mixture was allowed to react for 45 minutes. Finally, 39.5 grams triethylamine was added, and the prepolymer was dispersed with vigorous agitation into 179 g water, and diluted with a further 613 g of water. An additional 5.4 g of triethylamine was then added.

Example 20

A 2 liter reaction vessel, equipped with an agitator, heating mantle, and condensor, and nitrogen purge was charged with 76 g poly(propylene glycol) of 1025 molecular weight, and 42 g Synfac® 8031(Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 60° C. and 64 g acetone followed by 70 g 4,4'-methylenebis(phenylisocyanate) and 73.5 g 4,4'-methylenebis(cyclohexylisocyanate) were added. The mixture was allowed to react for 45 minutes. Finally, 39.5 grams triethylamine was added, and the prepolymer was dispersed with vigorous agitation into 179 g water, and diluted with a further 613 g of water. An additional 5.4 g of triethylamine was then added.

Example 21

A 2 liter reaction vessel, equipped with an agitator, heating mantle, and condensor, and nitrogen purge was charged with 76 g poly(propylene glycol) of 1025 molecular weight, and 42 g Synfac® 8031(Milliken Chemicals). The mixture was heated to 120° C. for 30 minutes and then cooled to 80° C. To the mixture, 47.5 g dimethylol propionic acid was added and allowed to disperse for 10 minutes. The mixture was cooled to 60° C. and 64 g acetone was added followed by 70 g 4,4'-methylenebis(phenylisocyanate). After 15 minutes, 73.5 g 4,4'-methylenebis (cyclohexylisocyanate) was added. The mixture was allowed to react for 20 minutes. Finally, 39.5 grams triethylamine was added, and the prepolymer was dispersed with vigorous agitation into 179 g water, and diluted with a further 613 g of water. An additional 5.4 g of triethylamine was then added.

Example 22

A 2 liter reaction vessel, equipped with an agitator, heating mantle, and condenser, and nitrogen purge was charged with 152 g poly(propylene glycol) of 1025 molecular weight, and 84 g Synfac® 8031(Milliken Chemicals). The mixture was heated to 120° C. for 30 minutes and then cooled to 80° C. To the mixture, 96 g dimethylol propionic acid was added and allowed to disperse for 10 minutes. The mixture was cooled to 70° C. and 266.4 g isophorone diisocyanate were added. The mixture was heated to 80° C. and allowed to react for 120 minutes. The prepolymer was dispersed with vigorous agitation into 35.82 g of NaOH dissolved in 1146.8 g of water.

Example 23

A 2 liter reaction vessel, equipped with an agitator, heating mantle, and condensor, and nitrogen purge was charged with 35 g poly(propylene glycol) of 1025 molecular weight, and 79 g of TONE 201 (polyester polyol from Union Carbide). The mixture was heated to 120° C. for 30 minutes and then cooled to 80° C. To the mixture, 46.9 g dimethylol propionic acid was added and allowed to disperse for 10 minutes. The mixture was cooled to 65° C. and 100 g isophorone diisocyanate was added. The reaction was allowed to rise to a temperature of about 80° C. The reaction was allowed to continue for about one hour and a half, 5.77% NCO, until 60% of the isocyanate reaction had taken place. The reaction mixture was cooled to about 65° C. and 38.96 grams triethylamine was then added. The prepolymer was then dispersed with vigorous agitation in 184.5 g of water. This was immediately followed by the addition of 250 g of water and 5.3 g of triethylamine. The resulting stable dispersion had a solids of 34.28%, viscosity of 90 cps and a pH of 9.

Comparative Example A

A 2 liter reaction vessel, equipped with an agitator, heating mantle, and condenser, and nitrogen purge was charged with 150 g poly(propylene glycol) of 2025 molecular weight. The mixture was heated to 120° C. for 30 minutes and then cooled to 80° C. To the mixture, 12 g dimethylol propionic acid was added and allowed to disperse for 10 minutes. The mixture was cooled to 60° C. and 66 g isophorone diisocyanate was added. The mixture was allowed to react for 3 hours at 80° C. Finally, 10 g triethylamine was added, and the prepolymer was dispersed with vigorous agitation into 464 g of water.

Preparation of Hair Compositions—Formulation and Performance Examples

Example 24

Hair Fixative Formulations

The polyurethanes from the previous examples were formulated into low VOC aerosol hair spray systems according to the following formulations. All values reported are parts by weight, based on the total weight of the hair spray composition.

| Ingredient | Parts by Weight (dry basis) | |
|---|---|---|
| | Alcohol-free (33% VOC) | 55% VOC |
| polyurethane polymer | 5.0 | 5.0 |
| anhydrous ethanol | — | 22.0 |
| deionized water | 62.0 | 40.0 |
| dimethyl ether | 33.0 | 33.0 |
| | 100.0 | 100.0 |

The polyurethane polymer, ethanol, and deionized water were mixed until homogeneous. Solutions were filtered and filled into aerosol containers. Cans were charged with dimethyl ether propellant. Hair spray formulations were tested for spray characteristics on 2 gram swatches of European brown hair. The sprays were delivered with a SEAQUIST NS-34 valve (0.013" vapor tap×0.013" stem orifice×0.040" dip tube diameter) having an EXCEL 200 MISTY (0.016" orifice) actuator in a 2 second burst from a distance of six inches. Formulas were compared to Control A (comparative example A in a 5% solids, 33% VOC aerosol) and Control B (commercially available VA/crotonates/vinyl neodecanoate copolymer in a 5% solids, anhydrous aerosol).

Example 25

Spray Characteristics Evaluations

The spray characteristics of the alcohol-free (33% VOC) and 55% VOC aerosols were rated an a scale from A to F, with A being the best spray. An "A" rating indicates a wide spray cone, fine spray, small particle size, and no foam on the hair or actuator. An "F" rating indicates a narrow spray cone, spitting at the actuator, large particle size, and obvious foaming on the hair or actuator. Mean particle size of the sprays were measured by a Malvern Series 2600 Droplet and Particle Size Analyzer from Malvern Instruments Inc. of Southborough, Mass. The results are listed in Table 1:

TABLE 1

| Spray Characteristics | | | |
|---|---|---|---|
| Polymer | % VOC Aerosol | Mean Particle Size ($\mu$) | Spray Rating |
| Example 6 | 33 | 31.34 | A |
| Example 7 | 33 | 35.87 | B+ |
| Example 8 | 33 | 29.43 | A |
| Example 9 | 33 | 40.66 | B+ |
| Example 10 | 33 | 33.51 | A− |
| Example 13 | 33 | 42.10 | B+ |
| Example 14 | 33 | 32.73 | A− |
| Example 15 | 33 | 32.27 | A− |
| Example 16 | 33 | 29.58 | A− |
| Control A | 33 | 48.40 | B+ |
| Example 6 | 55 | 45.25 | B+ |
| Example 7 | 55 | 41.42 | B |
| Example 8 | 55 | 34.94 | A− |
| Example 9 | 55 | 56.03 | C+ |
| Example 10 | 55 | 48.51 | C+ |
| Example 13 | 55 | 51.71 | B− |
| Example 14 | 55 | 44.87 | C+ |
| Example 15 | 55 | 42.58 | C+ |
| Example 16 | 55 | 46.81 | C+ |
| Control A | 55 | >150 | F |

The data clearly shows that these polymer examples provide acceptable sprayability in both water-based and water/alcohol-based aerosol systems, whereas the Control A has difficulty in spraying from systems that contain alcohol.

Example 26

Taber Stiffness Test Procedure

Alcohol-free aerosol hair spray formulations prepared from examples 5, 6, 7, and 8 as described in Example 24, were tested for stiffness on three 4¼" swatches of brown European virgin hair and the results pooled and averaged. The swatches were first dried in an oven at 110° F. for 30 minutes to remove moisture and then dried in a desiccator for 15 minutes. The swatches were weighed and the weight recorded as $W_1$. Each swatch was sprayed with a hair spray formulation for one second and then clipped to a retention board and dried in a 110° F. oven for 15 minutes. The swatches were cooled in the desiccator and reweighed. This weight was recorded as $W_2$. The swatches were then placed to equilibrate overnight at 50% relative humidity and 23° C.

Stiffness was tested using a Taber V-5 Stiffness Tester from Taber Industries of North Tonawanda, N.Y., designed for evaluating stiffness and resilience of paper, cardboard, and other flexible materials. The following procedure and calculation were adapted for use with hair samples.

When the machine is first turned on, the optical encoder inside the unit must be oriented before use. To do this, the driving disc was rotated left and right beyond the zero, using the control lever switch; then returned to zero.

Next, the pendulum was balanced by adjusting the levelers at the bottom of the two front legs until the line on the pendulum was directly under the zero line on the 100 graduation scale. The 500 unit weight was slid over the stud on the bottom of the pendulum. This weight multiplies each dial indication by five times.

The swatch was inserted between the clamp jaws, with the lower edge resting lightly on the bottom gauge. The clamp jaws were tightened by turning the screws on either side of the clamp.

The swatch was centered between the bottom rollers using the left screw to move the left hand roller until it makes contact with the swatch, but does not deflect the pendulum from zero. Then the right hand roller was brought into light contact with the swatch by using the right roller screw.

With one finger, light pressure was applied to the control lever switch and deflected the driving disc to the left until the line on the pendulum was under the 15° deflection mark.

The stiffness reading on the outer scale that falls opposite to the zero line on the driving disc (LS) was recorded. The same swatch was deflected to the right by 15° and that stiffness reading (RS) taken. The left and right readings were averaged and multiplied by five to give the stiffness value for that swatch. The results from the stiffness evaluations are listed in Table 2:

TABLE 2

Taber Stiffness Screening Test

| Polymer | Stiffness |
| --- | --- |
| Example 5 | 223 |
| Example 6 | 273 |
| Example 7 | 243 |
| Example 8 | 242 |
| Control A | 191 |
| Control B | 250 |

All polymer examples are superior in stiffness to Control A, and are equivalent in stiffness to control B.

Example 27

Removability Test Procedure

Using alcohol-free aerosol formulas, eight hair swatches were sprayed with the formulations described in Example 24 and eight with Control A and allowed to dry at ambient conditions for 1 hour. Each swatch was rinsed under tap water for 1 minute while working fingers into hair then dried in a 110° F. oven. The shampoo removability was determined and the results are shown in Table 3:

TABLE 3

Shampoo Removability Evaluations

| Polymer | Shampoo Removability |
| --- | --- |
| Example 6 | + |
| Example 7 | + |
| Example 8 | + |
| Exampte 9 | + |
| Example 10 | + |
| Example 14 | + |
| Example 16 | + |

A "+" indicates better results when compared with Control A. All examples have much improved removability from hair, and are superior to Control A.

Example 28

Curl Retention Test Procedure

Each of the alcohol-free aerosol formulations prepared from polymer examples 5, 6, 7, and 8 were tested on nine swatches of strands of Remi Blue String European Brown Hair for curl retention at 90% relative humidity, 22° C. (72° F.), and the results pooled and averaged. The testing procedure was as follows:

The hair was separated into swatches of approximately 2 grams in weight and bound at one end with cotton thread and epoxy glue. Each swatch was then washed in a 10% solution of shampoo, and rinsed in warm tap water. The hair was cut into 6 inch lengths from the secured end and dried at 49° C. (120° F.). The samples were wet again and combed, and the excess water squeezed out. The hair swatch was then rolled and secured onto a ½ inch diameter Teflon® mandrel, and dried at 49° C. (120° F.). When dried, it was removed from the mandrel and the resulting curl suspended by its bound end. For each swatch, the curl height was measured, and then the curl was sprayed uniformly. The curl was laid on a horizontal surface and allowed to air dry for one hour. The dried curl was then resuspended and set into a chamber at 22° C. (72° F.), 90% relative humidity, and the curl height measured immediately, and at 15, 30, 60 minute, 90 minute, and 2, 3, 4, 5, and 24 hour intervals.

The percentage curl retention was calculated by the formula $(L-L^t)/(L-L^\circ) \times 100$, where L is the length of hair fully extended, $L^\circ$ is the length of hair before spray and exposure, and $L^t$ is the length of hair after spray and exposure.

The results set out in Table 4 show that the hair fixative polymers and the alcohol-free aerosol formulations prepared from the polymers according to the methods of examples 5, 6, 7, and 8 effectively retained curl when compared to Control B.

TABLE 4

| Polymer | High Humidity (90%) Curl Retention Mean % Retention Values | | | | | | | | |
|---|---|---|---|---|---|---|---|---|---|
| | 15 min. | 30 min. | 60 min. | 90 min. | 2 hr. | 3 hr. | 4 hr. | 5 hr. | 24 hr. |
| Example 5 | 97.78 | 93.14 | 88.45 | 87.19 | 86.12 | 84.26 | 84.26 | 83.47 | 78.59 |
| Example 6 | 91.76 | 82.21 | 76.92 | 74.12 | 73.83 | 71.65 | 70.76 | 69.47 | 63.43 |
| Example 7 | 91.99 | 84.27 | 75.53 | 74.46 | 71.20 | 71.10 | 70.20 | 69.36 | 49.69 |
| Example 8 | 94.86 | 91.43 | 87.46 | 85.43 | 84.37 | 83.23 | 82.06 | 82.00 | 73.40 |
| Control B | 90.78 | 85.37 | 78.11 | 73.25 | 72.99 | 70.18 | 69.12 | 65.70 | 53.86 |

All of the examples are either equivalent or superior in humidity resistance when compared to Control B.

We claim:

1. A process for preparing a polyurethane polymer comprising dispersing the polymer in water after at least 50% of the theoretical isocyanate reaction has taken place, but before completion of the reaction, wherein the polyurethane polymer is prepared from
   a) monomers consisting essentially of:
   (i) one or more 2,2-hydroxymethyl-substituted carboxylic acids, represented by the formula

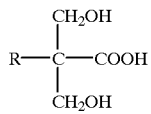

in which R represents hydrogen, or $C_1$–$C_{20}$ alkyl, present in a sufficient amount by weight to give 0.35–2.25 milliequivalents of carboxyl functionality per gram of polyurethane,
   (ii) about 5 to about 90% by weight, based on the weight of the polyurethane, of active hydrogen containing organic components, other than the 2,2-hydroxymethyl-substituted carboxylic acids, comprising a combination of at least one component (A) and at least one component (B); or at least one component (C) in combination with (A) and/or (B); or at least one component (C), wherein component (A) comprises a polymer with at least two active hydrogen atoms having a Tg less than 5° C.; component (B) comprises active hydrogen containing components comprising 5 to 14-membered rings, wherein the ring structure is heterocyclic, aliphatic, aromatic, cyclic, alicyclic, and/or spiro rings, and said 5–14 membered rings are substituted with zero to sixteen alkoxylate units; and component (C) comprises active hydrogen containing components comprising 5 to 14-membered rings, wherein the ring structure is heterocyclic, aliphatic, aromatic, cyclic, alcyclic, and/or spiro rings, and said 5 to 14 membered rings are substituted with greater than sixteen alkoxylate units; with the proviso that (A), (B), and (C) are non-halogentaed components,
   (iii) one or more organic diisocyanates present to react with the active hydrogens of the organic components, excepting the hydrogen on the carboxylate of the 2,2-hydroxymethyl-substituted caboxylic acid;
   (b) a diluent selected from the group consisting of
   (i) water,
   (ii) water and 0 to 90%, by weight of the diluent, of one or more organic solvents, and (iii) organic solvent.

2. A process for preparing a polyurethane polymer according to claim 1 wherein the dispersing step occurs after at least 70% of the theoretical isocyanate reaction has taken place, but before completion of the reaction.

3. The process according to claim 1 wherein the ratio of the isocyanate equivalents to reactive hydrogen equivalents in the polyurethane is less than, or equal to, 1.

4. The process according to claim 1 wherein the ratio of the isocyanate equivalents to reactive hydrogen equivalents in the polyurethane is greater than, or equal to 1.

* * * * *